United States Patent [19]

Gimesi et al.

[11] 4,445,927
[45] May 1, 1984

[54] HERBICIDAL COMPOSITIONS CONTAINING N-(PHOSPHONOMETHYL)-GLYCINE

[75] Inventors: Antal Gimesi, Budapest; József Baracskai, Balatonalmádi; Ferenc Fodor, Füzfögyártelep; Antal Gaál, Füzfögyártelep; András Horváth, Füzfögyártelep; Zoltán Kolonics, Galatonalmádi, all of Hungary

[73] Assignees: Nitrokemia Ipartelepek, Füzfögyártelep; Növenyvedelmi Kutato Intezet, Budapest, both of Hungary

[21] Appl. No.: 296,414
[22] PCT Filed: Dec. 23, 1980
[86] PCT No.: PCT/HU80/00012
    § 371 Date: Aug. 25, 1981
    § 102(e) Date: Aug. 25, 1981
[87] PCT Pub. No.: WO81/01787
    PCT Pub. Date: Jul. 9, 1981

[30] Foreign Application Priority Data

Dec. 28, 1979 [HU] Hungary .............................. NI 234

[51] Int. Cl.$^3$ ............................................. A01N 37/10
[52] U.S. Cl. ........................................ 71/86; 71/114; 71/117
[58] Field of Search .................................. 71/86, 114

[56] References Cited

U.S. PATENT DOCUMENTS 3,799,758  3/1974  Franz .................................... 71/86

Primary Examiner—Catherine L. Mills
Attorney, Agent, or Firm—Toren, McGeady and Stanger

[57] ABSTRACT

This invention relates to herbicidal compositions containing N-(phosphonomethyl)-glycine or a non-phytotoxic salt thereof, in combination with 2,4-dichlorophenoxyacetic acid or α-naphthylacetic acid or non-phytotoxic salt of these compounds.

By using the compositions according to the invention the herbicidally effective amount of N-(phosphonomethyl)-glycine can considerably be reduced in comparison with the commercially available compositions, which contain N-(phosphonomethyl)-glycine as an only active ingredient.

2 Claims, No Drawings

HERBICIDAL COMPOSITIONS CONTAINING N-(PHOSPHONOMETHYL)-GLYCINE

TECHNICAL FIELD

The invention relates to herbicidal compositions containing N-(phosphonomethyl)-glycine or a non-phytotoxic salt thereof, in combination with 2,4-dichlorophenoxyacetic acid or α-naphthylacetic acid or a non-phytotoxic salt of these compounds.

BACKGROUND ART

It is well known from the literature that N-(phosphonomethyl)-glycine can successfully be used for combatting weeds, especially perennial, deeply rooted weeds, but is effective also as a total plant killer U.S. Pat. No. 3,799,758.

2,4-Dichlorophenoxyacetic acid and α-naphthylacetic acid are also known in the art.

It is the object of the present invention to provide combinations, in which, as a result of using further additives, the herbicidally effective amount of N-(phosphonomethyl)-glycine can considerably be reduced in comparison with the herbicidally effective amount of N-(phosphonomethyl)-glycine in compositions, which contain this compound alone.

DISCLOSURE OF THE INVENTION

The present invention relates to herbicidal compositions comprising a combination of N-(phosphonomethyl)-glycine and 2,4-dichlorophonoxyacetic acid or α-naphthylacetic acid or a non-phytotoxic salt of these compounds, in an effective amount.

The present invention is based on the recognition that the herbicidally effective amount of N-(phosphonomethyl)-glycine or a salt thereof can considerably be reduced by using it in combination with 2,4-dichlorophenoxyacetic acid or a non-phytotoxic salt of these compounds.

Non-phytotoxic salts of N-(phosphonomethyl)-glycine preferably include alkyl amine salts, preferably having from 1 to 4 carbon atoms.

The preferred salts of 2,4-dichlorophenoxyacetic acid also include alkyl amine salts, preferably having from 1 to 4 carbon atoms, e.g. isopropyl amine, dimethyl amine salts, etc., but other salts, e.g. alkali metal, alkali earth metal salts can also be used.

The herbicidal compositions containing N-(phosphonomethyl)-glycine as active ingredient are commercially available generally as emulsifiable concentrates containing 30 to 36% by weight of active ingredient. They are generally employed at a rate of 10 lit./ha.

The compositions according to the invention contain from 0.01 to 95% by weight of the herbicidally active combination and 5 to 99.9% by weight of one or more formulation acids.

The total active ingredient concentration preferably is between 0.1 to 85% by weight, more preferably between 1 and 40% weight.

The proportion of N-(phosphonomethyl)-glycine to 2,4-dichlorophenoxyacetic acid or α-naphthylacetic acid can be varied within a wide range. The weight ratio of N-(phosphonomethyl)-glycine or a salt thereof to dichlorophenoxyacetic acid or a salt thereof preferably is between 5:1 and 1:5, more preferably between 4:1 and 1:2.

The proportion of N-(phosphonomethyl)-glycine or a salt thereof to α-naphthylacetic acid or a salt thereof preferably is between 2:1 and 5:1.

Is has surprisingly been found that of the herbicidal compositions according to the invention a smaller amount is required to obtain the same herbicidal effect than of the commercially available compositions, which contain N-(phosphonomethyl)-glycine as a sole active ingredient. In this way N-(phosphonomethyl)-glycine can partly be replaced by other agricultural chemicals and its effectivity can be increased.

The formulation aids usable in the compositions according to the invention are additives generally applied in the preparation of herbicides and described in detail in numerous textbooks. The formulation aids may for example be inert solid or liquid carriers, diluents, surfactants, e.g. dispersing and emulsifying agents, wetting agents, adhesives, etc.

As diluents for example various hydrocarbon derivatives, mineral oil fractions, vegetable and animal oils, polar solvents, water, etc. can be used. By using these formulation aids the compositions may conveniently be formulated as solutions, emulsions and dispersions.

The compositions according to the invention may also be formulated as concentrates, which can be diluted in the place of application with water or any other suitable solvent. Such concentrates include for example pastes, oily dispersions, emulsifiable concentrates, etc.

Suitable surfactants include salts of ligninsulfonic acid, alkylaryl sulfonates, alkyl sulfates, fatty alcohol sulfates, alkylarylpolyglycol ethers, etc.

BEST MODE OF CARRYING OUT THE INVENTION

The present invention and the best modes of carrying out the invention are illustrated in detail by the following Examples which do not however serve to limit the scope of protection sought.

EXAMPLE 1

Field trial

Test Plants:
 Agropyron repens,
 Cynodon dactylon and
 Sorghum halepense
 (perennial, monocotyledonous weeds)

Test compounds:
 A N-(phosphonomethyl)-glycine
 E 2,4-dichlorophenoxyacetic acid dimethyl amine salt
 F α-naphthylacetic acid Field trials were carried out with the following compositions:

A dispersion of 1.8 and 3.6 kg of compound A in 500 lit. of water is applied to one hectare.

In another test a dispersion of 1.8 kg of a compound A and 0.9 kg of a compound E or F in 500 lit. of water was applied to one hectare.

Control experiments were carried out also with compositions containing 0.9 kg of compound E and F, respectively.

Evaluation was made 30 days after treatment.

The results obtained are given in the following Table 1.

TABLE 1

| Plant | Active ingredient (kg/ha.) | | | | | |
|---|---|---|---|---|---|---|
| | A | E | F | A + E | A + F |
| | 1.8 | 3,6 | 0.9 | 0.9 | 1.8 + 0.9 | 1.8 + 0.9 |
| *Agropyron repens* | 65 | 100 | 0 | 0 | 100 | 100 |
| *Cynodon dactylon* | 60 | 95–100 | 0 | 0 | 100 | 100 |
| *Sorghum halopense* | 65 | 100 | 0 | 0 | 100 | 100 |

0 = no damage
100 = total killing.

From the data given above it can be seen that the compositions containing a combination of compounds A and E, and A and F, respectively, have the same effect as the compositions containing N-(phosphonomethyl)-glycine (compound A) alone, in an amount of 3.6 kg. In other words, when using the combination according to the invention the amount of N-(phosphonomethyl)-glycine required to achieve the same herbicidal effect is reduced by 50%.

EXAMPLE 2

Field Trials

Test plants:
 Agropyron repens,
 Ciochorium intybus,
 Plantago media,
 Cynodon dactylon,
 Achilles distans,
 Artemisia vulgaris,
 Sochus oleraceus.

Test compounds:
 A N-(phosphonomethyl)-glycine,
 E 2,4-dichlorophenoxyacetic acid dimethyl amine salt.

Field trials were carried out with the following compositions:

A dispersion of 1.08 kg. of compound A and compound E, respectively in 500 lit. of water; and a dispersion of a combination of 0.6 kg. of compound A and 0.2 kg. of compound E in 500 lit. of water.

45 days after spraying it was established that the composition containing a combination of the compounds A and E had the same herbicidal effect on all test plants as the composition containing N-(phosphonomethyl)-glycine alone, i.e. necessary amount of N-(phosphonomethyl)-glycine can be reduced to about 60%.

Analogeous tests were carried out also Agropyron repens, Achilles distans, Artemisia vulgaris, Cynodon dactylon, Plantago media and Sonchus oleraceus. If was found that a dispersion of 1.8 kg. of N-(phosphonomethyl)-glycine in 500 lit. of water resulted in killing of 70% of the weeds 30 days after treatment, while when adding also 10, 20 and 40% by weight, respectively of 2,4-dichlorophenoxyacetic acid to the compositions, the weed-killing was about 85 to 95%.

EXAMPLE 3

Emulsifiable concentrates

| Ingredients | Amount (parts by weight) |
|---|---|
| 1:1 mixture of N—(phosphonomethyl)-glycine and 2,4-dichlorophenoxy-acetic acid dimethyl amine salt | 10 |
| Isooctylphenol polyglycol ether | 10 |
| Water | 80 |

The mixture obtained by admixing the ingredients, optionally immediately before application, is diluted with water to the desired concentration.

EXAMPLE 4

Aqueous dispersion

| Ingredients | Amount (parts by weight) |
|---|---|
| 2:1 mixture of N—(phosphonomethyl)-glycine and 2,4-dichlorophenoxyacetic acid dimethyl amine salt | 30 |
| Xylene | 80 |
| Ethyleneoxide-oil acid N—monoethanol amide addition product | 10 |
| Dodecylbenzenesulfonic acid Ca | 5 |
| Ethyleneoxide-castor oil addition product | 5 |

The dispersion obtained by admixing the ingredients is diluted with 100 000 parts by weight of water.

EXAMPLE 5

Tank mixture

| Ingredients | Amount (parts by weight) |
|---|---|
| 1:2 mixture of N—(phosphonomethyl)-glycine and 2,4-dichlorophenoxy-acetic acid dimethyl amine salt | 10 |
| 2,4-dichlorophenoxyacetic acid dimethyl amine salt | 10 |
| ligninesulfonic acid Na | 10 |

The mixture obtained by admixing the ingredients is diluted with 10 000 parts by weight of water. The tank mixture contains 0.1% weight of active ingredient.

What we claim is:

1. Herbicidal compositions comprising a combination of N-(phosphonomethyl)-glycine and α-naphthylacetic acid in a ratio in the range from 2:1 to 5:1 or a non-phytotoxic salt of these compounds.

2. The composition of claim 1 containing from 0.01 to 95% by weight of said herbicidally active combination and 5 to 99.9% by weight of one or more formulation aids.

* * * * *